United States Patent [19]

Cooper et al.

[11] Patent Number: 5,572,031
[45] Date of Patent: Nov. 5, 1996

[54] PRESSURE- AND TEMPERATURE-COMPENSATING OXYGEN SENSOR

[75] Inventors: David E. Cooper; Jan E. ver der Laan, both of Palo Alto; Haris Riris; Clinton B. Carlisle, both of Menlo Park, all of Calif.

[73] Assignee: SRI International, Menlo Park, Calif.

[21] Appl. No.: 344,765

[22] Filed: Nov. 23, 1994

[51] Int. Cl.$^6$ .......................... G01J 3/433; G01N 21/00; G01D 21/02
[52] U.S. Cl. .......................... 250/343; 250/345; 250/346; 250/351; 356/437
[58] Field of Search ................... 250/343, 345, 250/346, 351; 356/437

[56] References Cited

U.S. PATENT DOCUMENTS

| | | | |
|---|---|---|---|
| 3,524,066 | 8/1970 | Blakkan. | |
| 4,119,408 | 10/1978 | Matson | 422/169 |
| 4,356,065 | 10/1982 | Dietz | 204/1 T |
| 4,410,273 | 10/1983 | Mantz et al. | 356/319 |
| 4,730,112 | 3/1988 | Wong | 250/343 |
| 5,173,749 | 12/1992 | Tell et al.. | |
| 5,178,267 | 1/1993 | Grabenkort et al. | 206/210 |
| 5,222,389 | 6/1993 | Wong | 73/31 |
| 5,317,156 | 5/1994 | Cooper et al. | 250/343 |
| 5,340,986 | 8/1994 | Wong | 250/343 |
| 5,340,987 | 8/1994 | Eckles et al. | 250/345 |
| 5,448,071 | 9/1995 | McCaul et al. | 250/343 |

FOREIGN PATENT DOCUMENTS

| | | |
|---|---|---|
| 59-56151 | 9/1992 | Japan. |
| 2165640 | 4/1986 | United Kingdom. |
| 2219656 | 12/1989 | United Kingdom. |
| 2258529 | 10/1993 | United Kingdom. |

Primary Examiner—Constantine Hannaher
Assistant Examiner—Virgil O. Tyler
Attorney, Agent, or Firm—David G. Beck; Townsend and Townsend and Crew LLP

[57] ABSTRACT

RF modulation spectroscopy of a near-infrared tunable laser diode source is used to determine the oxygen concentration in a sample medium. A reference cell containing a known concentration of oxygen is used to calibrate the apparatus as well as to lock the laser on an oxygen absorption line. The temperature of the reference cell is monitored from which the pressure in the reference cell can be determined. Both the temperature and the pressure in the sample cell are monitored, either directly using independent transducers or indirectly using spectroscopic techniques. The oxygen content of the sample is determined, correcting for both temperature and pressure effects.

15 Claims, 12 Drawing Sheets

PRESSURE- AND TEMPERATURE-COMPENSATING OXYGEN SENSOR

BACKGROUND OF THE INVENTION

The present invention relates generally to oxygen measurement devices, and more specifically to an oxygen sensor for aircraft fuel tanks.

Aircraft air/fuel mixtures are explosive at oxygen concentrations above approximately 12 percent, therefore it is desirable to monitor and control the oxygen concentration in fuel tanks in order to avoid explosions. These explosions may be due to lightning strikes, electrical shorts, static electricity and, in the case of military aircraft, hostile combat environments. Although some fuels are less volatile, additional fuel tank protection is still desirable. One approach to obtaining fuel tank protection is through fuel tank inerting.

There are two basic techniques in use or under development for modern aircraft fuel tank inerting; first, on-board liquid nitrogen systems and second, on-board inert gas generation systems (OBIGGS). The former approach is cost prohibitive for many applications, primarily due to the extensive ground support required (e.g., special nitrogen servicing trucks and liquid nitrogen storage tanks). The primary concerns with regards to self-generating systems are the cost and weight aspects as well as their ability to supply sufficient inert gas to repressurize the fuel tanks during each descent.

In either of the fuel tank inerting systems described above it is desirable to monitor the oxygen content of the fuel tank and the inerting system supply gas, thus indicating both the relative flammability of the fuel vapor mixture and the effectiveness of the inerting system. The extremely hostile environment of the aircraft as well as the need for high accuracy, stability, and freedom from interference make the use of electro-chemical sensors impractical. Furthermore, a suitable oxygen monitor must be able to both survive and correct for the rapid and extreme pressure and temperature changes common to aircraft flights.

Tell et al. (U.S. Pat. No. 5,173,749) describe a method and apparatus for making spectroscopic measurements of the concentration of a gas in a sample cell using a modulated laser diode as the light source. Applicability of this apparatus to both medical and industrial applications is described. The '749 patent does not disclose how to correct for or measure either temperature or pressure using a single spectroscopic instrument.

SUMMARY OF THE INVENTION

The present invention provides an accurate means of measuring the oxygen content in a sample medium, correcting for both temperature and pressure.

In brief, the present invention utilizes RF modulation spectroscopy of a near-infrared tunable laser diode source to determine the oxygen concentration in a sample medium. A reference cell containing a known concentration of oxygen is used to calibrate the apparatus as well as to lock the laser on an oxygen absorption line. The temperature of the reference cell is monitored, which allows the pressure in the reference cell to be determined. The temperature and the pressure in the sample cell are also monitored, either directly using independent transducers or indirectly using spectroscopic techniques. The oxygen content of the sample is determined, correcting for both temperature and pressure effects.

In one embodiment of the invention a probe containing both a sampling cell and a reference cell is connected via fiber optics to a remotely mounted electronics package. The probe, also containing temperature and pressure sensors, is designed to fit within an aircraft fuel tank in order to measure the tank's oxygen content. The electronics package, due to its remote mounting, need not be hermetically sealed to prevent damage from the fuel, is not subjected to the variations in temperature and pressure experienced inside the tank, and is easier to service and calibrate.

DESCRIPTION OF SPECIFIC EMBODIMENTS

OVERVIEW OF FREQUENCY MODULATION SPECTROSCOPY (FMS) AND WAVELENGTH MODULATION SPECTROSCOPY (WMS)

Two types of laser absorption spectroscopy, referred to as Frequency Modulation Spectroscopy (FMS) and Wavelength Modulation Spectroscopy (WMS), will be described. In laser absorption spectroscopy, a signal of interest results from the interaction of a probing field with a sample. This field is the laser beam, the wavelength of which is nearly resonant with an absorption line of the sample.

Figure 1A:
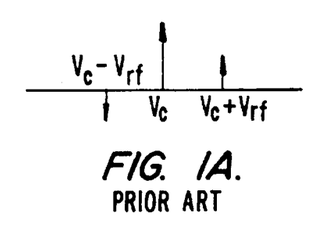
FIGS. 1A–B illustrate an RF modulation technique for use with the present invention.
Figure 1B:
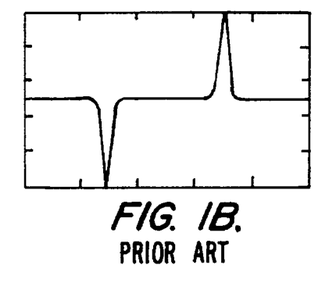

FIGS. 1A–B illustrate schematically certain characteristics of FMS. FMS calls for the modulation of a laser at high frequencies (in the tens of MHz to GHz range), either by an external electro-optic modulator, or as in the case of laser diodes, by modulating the injection current. The modulated laser beam is passed through a sample, and the transmitted beam is demodulated using a fast photodetector and suitable processing electronics.

In frequency space, the modulated laser field consists of a carrier frequency, which is the natural emission frequency of the laser, and sidebands displaced from the carrier by integral multiples of the modulation frequency. In the weak modulation limit the laser spectrum can be approximated by the first set of sidebands (FIG. 1A). For no absorption, the beat signal from the carrier and the upper sideband exactly cancels the beat signal from the carrier and the lower sideband because they have the same amplitude and are exactly 180° out of phase. If, prior to detection, the laser beam propagates through a medium containing molecules that preferentially absorb one of the sidebands, then the two beat tones no longer cancel, and a signal that resembles a first derivative of the absorption lineshape results (FIG. 1B). Although demodulation is usually performed at the modulation frequency, it can be performed at a harmonic of the modulation frequency.

FMS offers advantages over direct absorption techniques. Direct absorption methods detect the signal as a change in the laser intensity and have their detection bandwidth in a region of the frequency spectrum where there is a large 1/f noise component. FMS detects the signal at the modulation frequency, where most lasers exhibit very little 1/f noise. Since the signal in FMS results from the differential absorption of the sidebands, for maximum sensitivity the modulation frequency should be comparable to the linewidth of the absorption.

Figure 2A:
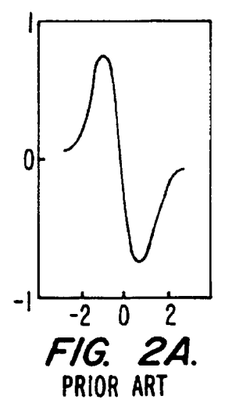
FIGS. 2A–B illustrate the first and second harmonic signals recovered using the WMS modulation technique.
Figure 2B:
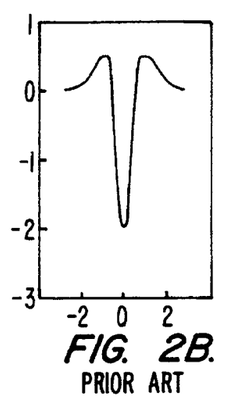

WMS predates the FMS techniques described above, and has been used with tunable diode laser sources since the late 1960's. It is an outgrowth of modulation techniques that were originally used to enhance the sensitivity of signals in nuclear magnetic resonance (NMR) and electron paramagnetic resonance (EPR) spectroscopy. The methods were in use during the 1950's in NMR and EPR. In NMR and EPR the probing field is an RF electromagnetic field that is nearly resonant with the nuclear or electron spins of the sample. In WMS (and FMS) this field is the laser beam, the wavelength of which is nearly resonant with an absorption line of the sample. In general, one recovers signals from the resonance at all harmonics of the modulation frequency. Usually only the first and second harmonic signals are recorded, and they are proportional to the first and second derivatives of the resonant lineshape (FIGS. 2A–B).

In WMS, modulation frequencies in the kHz region have been traditionally used for sensitive spectroscopic detection. However, with the development of FMS in the 1980's, the advantages of modulation and detection in the MHz region have been appreciated, and WMS at MHz frequencies has been demonstrated. The differences between FMS and WMS are slight. In FMS, the modulation index of the laser is less than or equal to one, but the ratio of the modulation frequency to the width of the absorption feature is greater than or equal to one. As a result, the absorption feature of interest is probed with a single isolated sideband or a small set of sidebands. In WMS the ratio of the modulation frequency to the width of the absorption feature is much smaller than 1, but the modulation index is very large. As a result, the absorption feature is probed with a large number of sidebands. Thus, FMS and WMS may be viewed as limiting cases of a more general modulation spectroscopy.

COMPENSATION FOR PRESSURE AND TEMPERATURE EFFECTS

In laser absorption spectroscopy the signal of interest is the total absorption experienced by a laser beam traversing a gas sample. According to Beer-Lambert law, light of intensity $I_o$ traversing a path D in an absorbing gas of number density N and absorption cross-section $\sigma$ is attenuated exponentially, $$I = I_o \exp(-N\sigma D)$$

The resulting change in intensity can then be written as, $$\Delta I = (I_o - I) = I_o\{1 - \exp(-N\sigma D)\} \approx I_o N\sigma D$$

where the last step follows for the case of small absorptions. In modulation spectroscopy the light traversing the sample is directed onto a photodetector, and the source is modulated in such a way that the detector photocurrent contains both ac and dc components. Generally the dc component is proportional to the total optical power impinging on the detector and the ac component is proportional to the change in intensity resulting from the presence of the absorbing sample. Explicitly, we can write, $$i_{dc} = a g_{dc} I = a g_{dc} I_o \exp(-N\sigma D) \approx a g_{dc} I_o$$

$$i_{ac} = a J g_{ac} \Delta I \approx a J g_{ac} I_o N\sigma D$$

where a is an optical attenuation factor that includes window transmission, mirror reflectivity, etc., all of which may change over time, J is a function dependent on the modulation amplitude of the diode laser and on the width of the absorption line measured by the modulation technique, and g is an electronic gain factor which includes the detector responsivity (which may be different for the dc and ac signals), as well as the total electronic gain. To normalize out the system constants a and $I_o$, it is useful to form the ratio of the ac to dc signals. This gives, $$W = i_{ac}/i_{dc} = J(g_{ac}/g_{dc})N\sigma D = JGN\sigma D$$

In the present invention, this normalized signal will be collected from the reference cell as well as any sample cells. Using a subscript to distinguish between these and including the implicit temperature and pressure dependence of the various factors in this equation gives, $$W_i = J_i G_i N_i \sigma D_i = J(T_i,P_i) G_i N_i (T_i,P_i) \sigma(T_i,P_i) D_i$$

In the last step we have dropped subscripts from J and $\sigma$ because they are presumably known universal functions of temperature and pressure (this is also true of N, but because the molecular number density can be different for each sample we keep the index in this case). Letting subscripts 1 and 2 denote the reference and sample gas, we form ratios of the unknown sample signals to the reference signal, $$R_2 = W_1/W_2 = \frac{J(T_2,P_2)G_2N_2(T_2,P_2)\sigma(T_2,P_2)D_2}{J(T_1,P_1)G_1N_1(T_1,P_1)\sigma(T_1,P_1)D_1}$$

Next we need to include the fact that some of the factors in these equations are known universal functions of temperature and pressure. Explicitly, we have $$N(T,P) = N(T_o,P_o)(P/P_o)(T_o/T)$$

$$\sigma(T,P) = \sigma(T_o,P_o)(P_o/P)(T_o/T)^n \exp\{-E_o(1/kT - 1/kT_o)\}$$

where $T_o$ and $P_o$ are a convenient reference temperature and pressure, $E_o$ is the ground state energy of the transition responsible for the absorption, and the exponent n is equal to 0.5 from kinetic theory, but deviates from this value for certain gases. For pure oxygen, n=0.3. Inserting these expressions in the numerator and denominator of the above expressions for the ratio $R_2$ gives, $$R_2=(J_2/J_1)(G_2/G_1)\{N_2(T_o,P_o)/N_1(T_o,P_o)\}*(T_1/T_2)^{n+1}(D_2/D_1)\exp\{-E_o(1/kT_2-1/kT_1)\}$$

These signal ratios, formed from the two measurements $W_1$ and $W_2$ are the numbers from which the oxygen volume fraction is easily computed, as shown below.

The volume fraction f may be defined as the ratio of the number density of the gas of interest to the number density of an ideal gas at the same temperature and pressure. This latter number is sometimes referred to as Loschmidt's number when the temperature is 0° C. and the pressure is 1 atmosphere $\{N_L(0,1 \text{ atm})=2.68719\times10^{19} \text{ molecules/cm}^3\}$. Mathematically, $$f=N(T,P)/N_L(T,P)=N(T_o,P_o)/N_L(T_o,P_o)$$

where the last step follows from the ideal gas law. Solving for $N_2$ in the above expressions for $R_2$ and dividing by Loschmidt's number gives our basic expressions for the volume fraction in the unknown sample, $$\begin{aligned}f_2 &= N_2(T_o,P_o)/N_L(T_o,P_o)\\&= R_2(J_1/J_2)(G_1/G_2)\{N_1(T_o,P_o)/N_L(T_o,P_o)\}*\\&\quad (T_2/T_1)^{n+1}(D_1/D_2)\exp\{-E_o(1/kT_1-1/kT_2)\}\end{aligned}$$

With the exception of the signal ratios R, the modulation coefficients J, and the temperature, the factors in these equations are constants that are known or can be determined at the time of instrument setup and calibration.

In the present invention, we are free to choose a number of the constants that appear in the above equations. Specifically, we can choose the concentration of oxygen in our reference cell to be equal to Loschmidt's number, we can make all of the optical path lengths identically equal, and we can match the electronic gains. With these constants, the above expressions reduce to, $$f_2=R_2(J_1/J_2)(T_2/T_1)^{n+1}\exp\{-E_o(1/kT_1-1/kT_2)\}$$

Consequently, the measurements of the two signals $W_1$ and $W_2$ and the two corresponding temperatures $T_1$ and $T_2$ and knowledge of the two J factors are sufficient for determination of the oxygen volume fraction in the unknown sample, provided the other system constants are known and do not drift.

Figure 3:
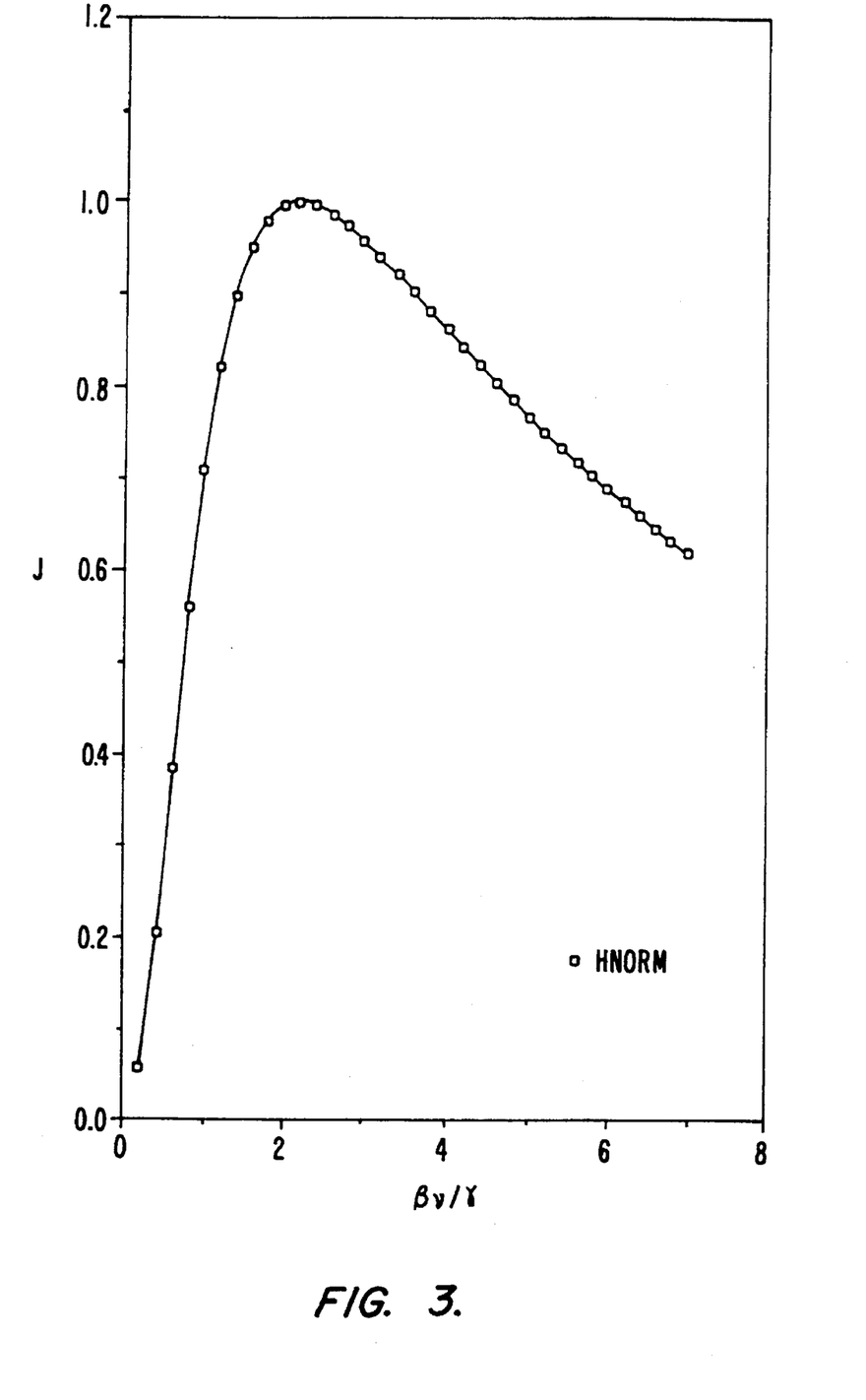
FIG. 3 is a plot of the WMS second harmonic signal amplitude versus the ratio of the frequency modulation index times the modulation frequency to the halfwidth of the gas absorption line for a lorentzian lineshape.

The J coefficients can be derived from the theory of wavelength modulation spectroscopy (WMS). For second harmonic detection where the lineshape is well approximated by a lorentzian, J is simply a function of the dimensionless ratio of the product of the modulation amplitude, $\beta$, and the modulation frequency, $\upsilon$, of the laser diode, to the halfwidth, $\gamma$, of the gas absorption line. In terms of $x=\beta\upsilon/\gamma$, for a lorentzian lineshape J is approximate by, $$J(x)=(4/x^2)-(2/x^2)(2+x^2)/(1+x^2)^{1/2}$$

This function has a maximum at $x=2.2$, and is plotted in FIG. 3. Since the gas absorption line width is pressure dependent according to, $$\gamma(T,P)=\gamma(T_o,P_o)(P/P_o)(T_o/T)^{1-n}$$

we see that J is also pressure dependent. Thus, in order for the present oxygen sensor to accurately measure the oxygen volume fraction, it must also measure the pressure, $P_2$, of the unknown sample. Since the reference cell volume is fixed, the reference gas pressure may be determined from a temperature measurement using the ideal gas law. Thus $J_1$ can be determined from the diode laser modulation amplitude and frequency and the reference cell gas temperature $T_1$. In actual practice it is most convenient to adjust $\beta\upsilon$ so that $x=2.2$ for a gas sample at atmospheric pressure and room temperature ($T_o=296°$ K.).

OXYGEN SENSOR APPARATUS

Figure 4:
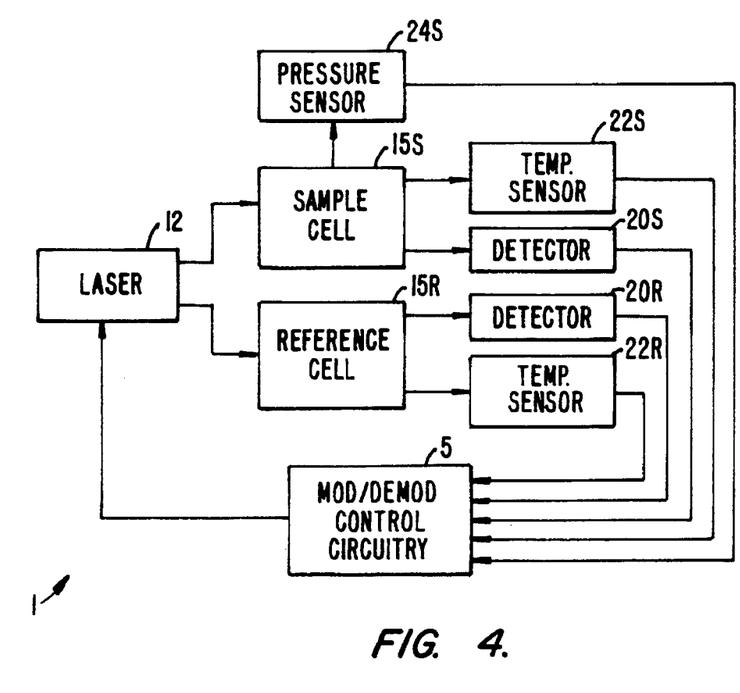
FIG. 4 is a high level optical and electrical block diagram of apparatus according to the invention.
Figure 5:
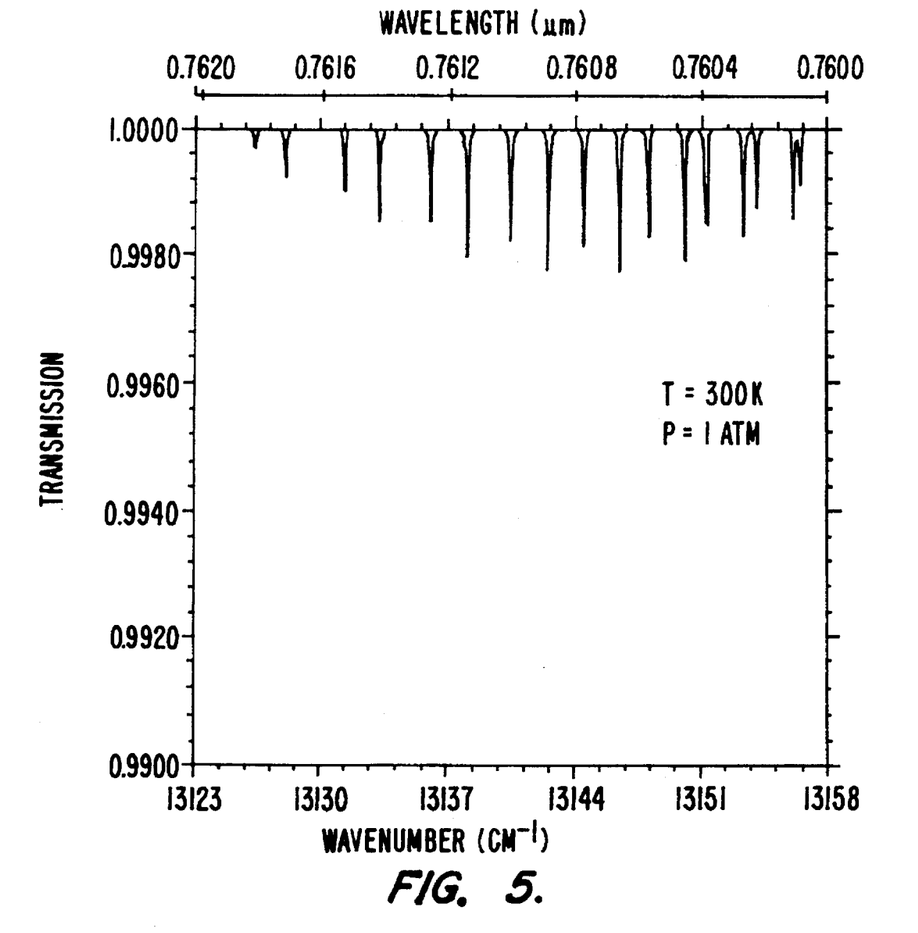
FIG. 5 is a plot of the absorption spectrum of oxygen at approximately 0.76 micrometers.

FIG. 4 is a high level optical and electrical block diagram of apparatus 1 for measuring the oxygen concentration in a sample cell. A modulation control circuit 5 provides RF modulation to a tunable laser diode 12 operating at a wavelength of approximately 0.76 micrometers. Oxygen has a number of strong absorption lines in this wavelength region (see FIG. 5). The modulated output of laser 12 is sent through a reference cell 15R and a sample cell 15S. Associated with the reference and sample cells are detectors 20R and 20S which provide a signal representing the intensity of the laser beam transmitted through the associated cell. Control circuit 5 processes the signals from detectors 20R and 20S and from this information, combined with the temperature and pressure information provided by temperature sensors 22R and 22S and pressure sensor 24S, computes the oxygen concentration in sample cell 15S.

The information provided by sensors 22S and 24S can also be determined spectroscopically (not shown). Because the width and strength of the oxygen absorption lines vary with pressure and temperature in a known way, accurate measurement of the line widths and intensities of two different oxygen absorption lines allows the temperature and pressure to be determined, thereby eliminating the need for temperature sensor 22S and pressure sensor 24S. The line width effect is due to broadening of the molecular electronic transition by collisions with other molecules, and is the dominant broadening effect for pressures ranging from around 20 torr up to many atmospheres. The line strength effect is due to the fact that the ground state of the transition responsible for each oxygen absorption line in the 760 nm region corresponds to a different molecular rotational level, and at any given temperature the ground state population is different for the different rotational levels. Since the line strength is proportional to the ground state population, it is temperature dependent in a way that depends on the ground state energy.

Figure 6:
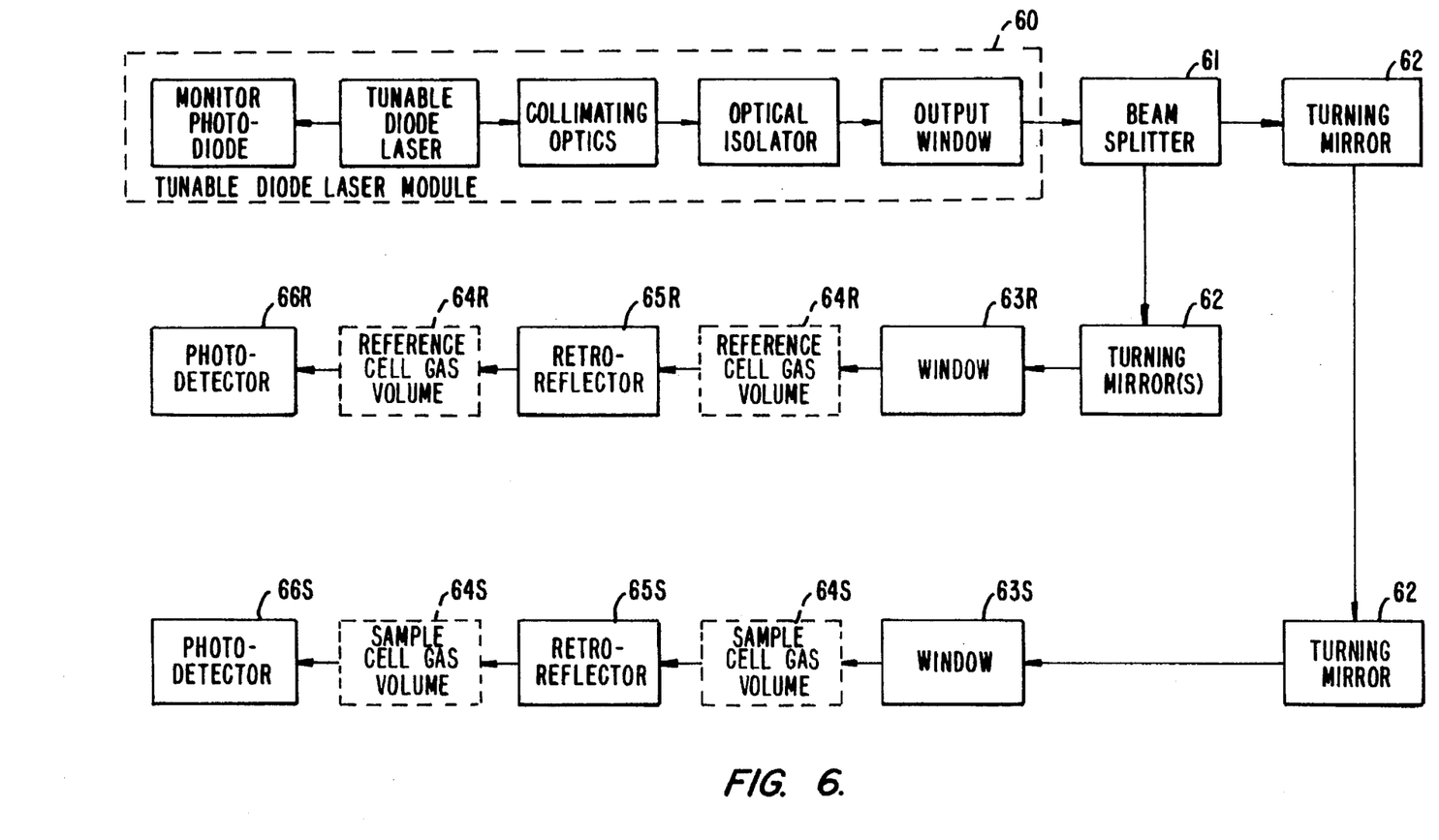
FIG. 6 is a schematic of the optical train of a first embodiment of the invention.
Figure 7:
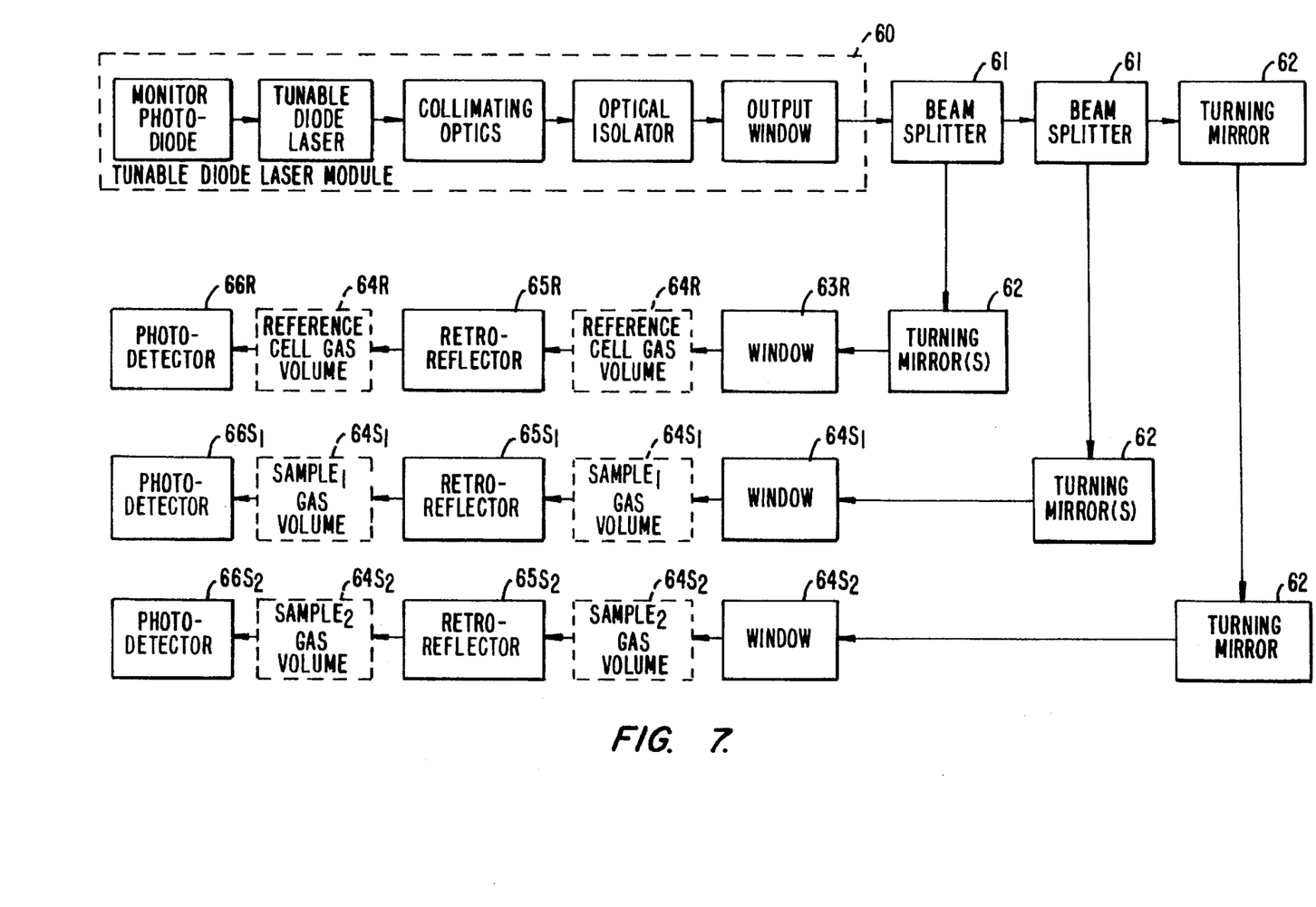
FIG. 7 is a schematic of the optical train of a second embodiment of the invention.

FIG. 6 is an optical schematic showing one embodiment of the optical train according to the invention. In this embodiment there is only a single sample cell. The laser beam exiting a tunable diode laser module 60 is split at a beam splitter 61 into two beams. Turning mirrors 62 direct the first beam into a reference gas cell and the second beam into the medium to be measured. In this embodiment the optical path through the reference cell 64R and the sample cell 64S are identical: the interrogation beam enters the cell through window 63R/63S; passes through cell 64R/64S; is reflected back by retro-reflector 65R/65S; passes through cell 64R/64S again; and impinges on detector 66R/66S. FIG. 7 shows a second embodiment of the invention. This embodiment is similar to that shown in FIG. 6 except that the laser beam is split into three beams, thereby allowing two different samples to be interrogated in addition to the reference cell.

Figure 8:
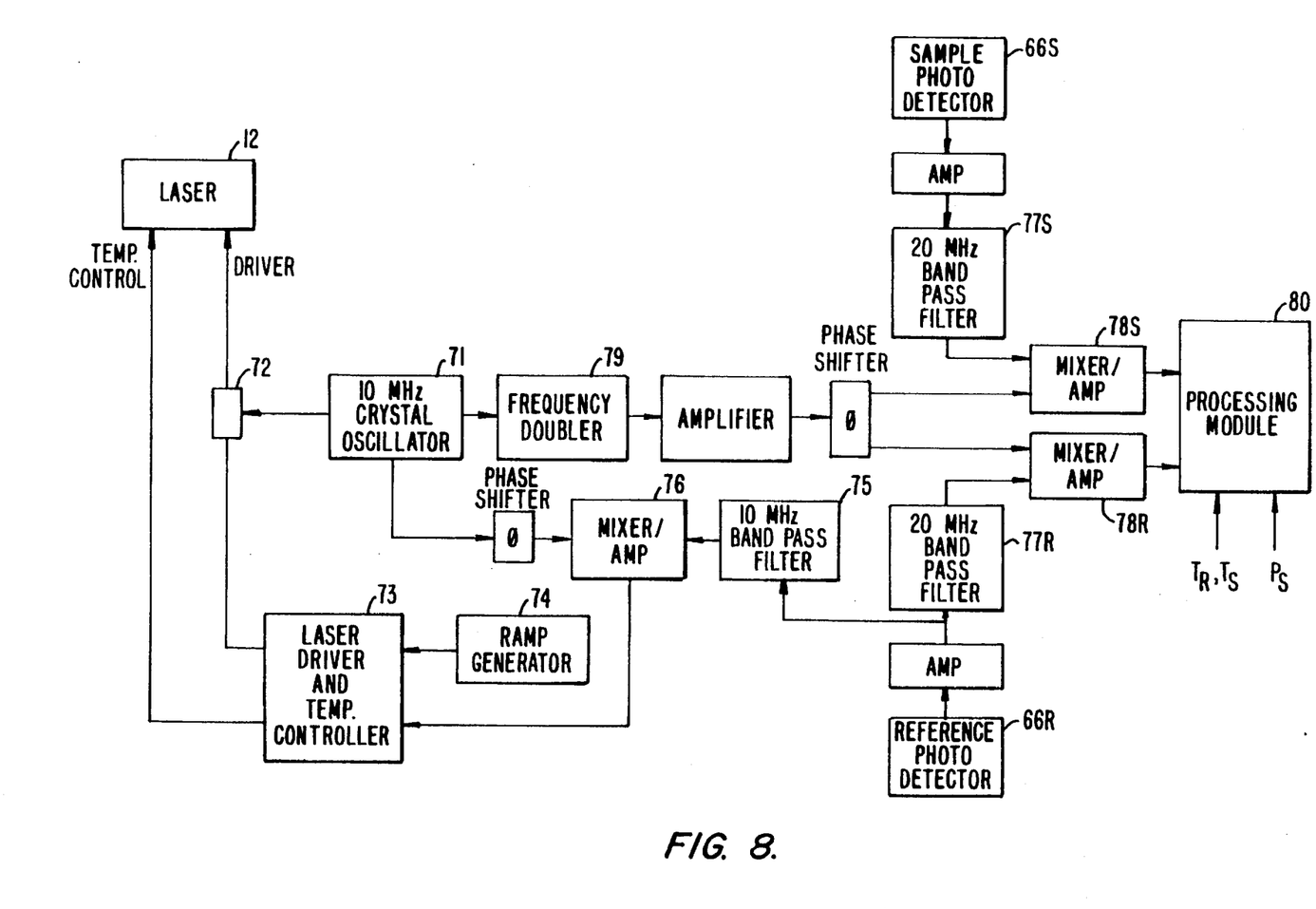
FIG. 8 is a block diagram of control circuitry for an embodiment using a single sample cell.

FIG. 8 is a block diagram of control circuitry for an embodiment using a single sample cell. A crystal oscillator 71 provides a signal at a single modulation frequency; 10

MHz is representative. A portion of the signal generated by the crystal oscillator is coupled to diode laser 12 through a bias tee or network 72 to modulate the laser drive current. The purpose of network 72 is to combine both the high and low frequency components of the injection current drive. These components include the dc forward bias that drives the laser and is provided by a laser driver 73, the low frequency ramp signal provided by a ramp generator 74, and the rf signal.

Light emitted by laser 12 passes through reference cell 64R and sample cell 64S, and is then detected by photodetectors 66R and 66S, respectfully. After amplification the signal from reference photodetector 66R is split and one portion of the signal is passed through a 10 MHz band pass filter 75. This signal and one from 10 MHz oscillator 71 are applied to a mixer 76, the output of which is used to line-lock the laser diode. The other signal from reference detector 66R as well as the signal from sample detector 66S are passed through 20 MHz band pass filters 77R/77S and applied to the RF inputs of mixers 78R/78S. A second portion of the 10 MHz oscillator signal is passed through a frequency doubler 79 and applied to the LO inputs of mixers 78R/78S. The analog output of mixers 78R/78S is communicated to a processing module 80 where the output is digitized along with the temperature and pressure information from the cells. Module 80 computes the oxygen concentration in the sample cell.

Figure 9:
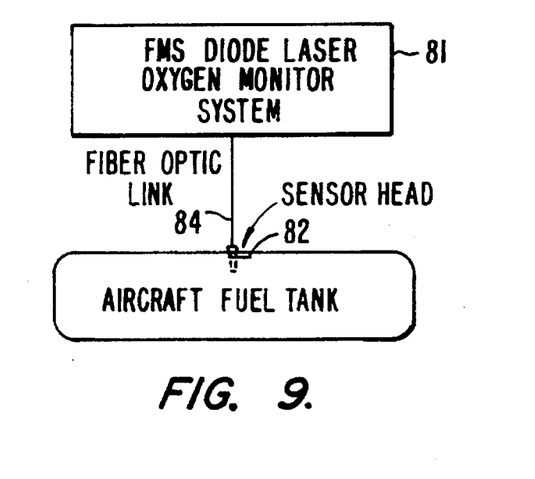
FIG. 9 illustrates an embodiment of the invention using a remote probe.
Figure 10:
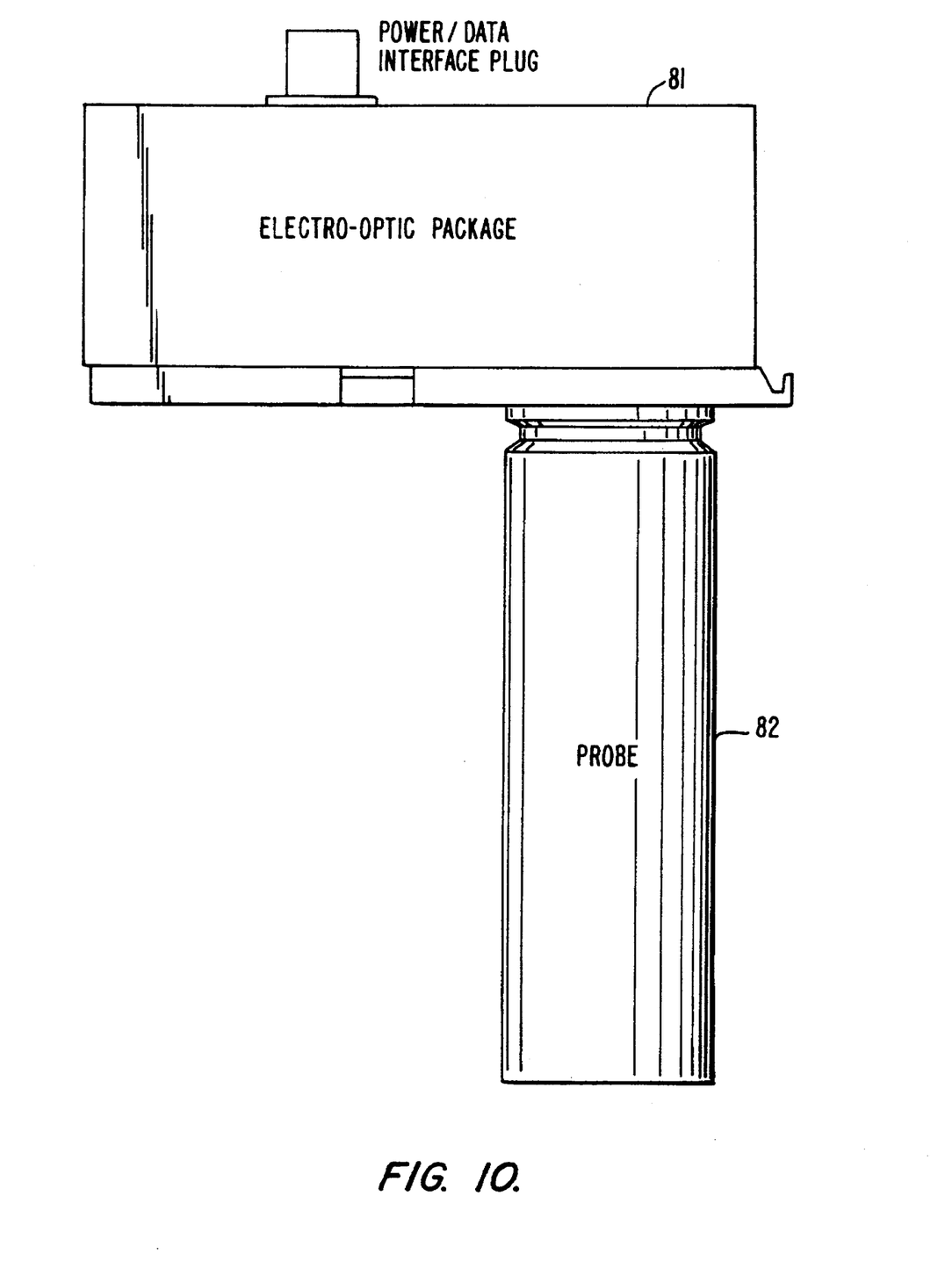
FIG. 10 illustrates an embodiment of the invention in which the oxygen sensor assembly includes both the electro-optic housing and the probe housing.

FIGS. 9–10 illustrate two embodiments of the invention. In both embodiments there is an electro-optic package 81 and a sensor probe 82. In the embodiment shown in FIG. 9, package 81 and probe 82 are separated by a fiber optic link 84. Fiber optic link 84 allows probe 82 to measure the oxygen concentration in a remote environment, possibly one which is potentially hostile to electronics.

Figure 11:
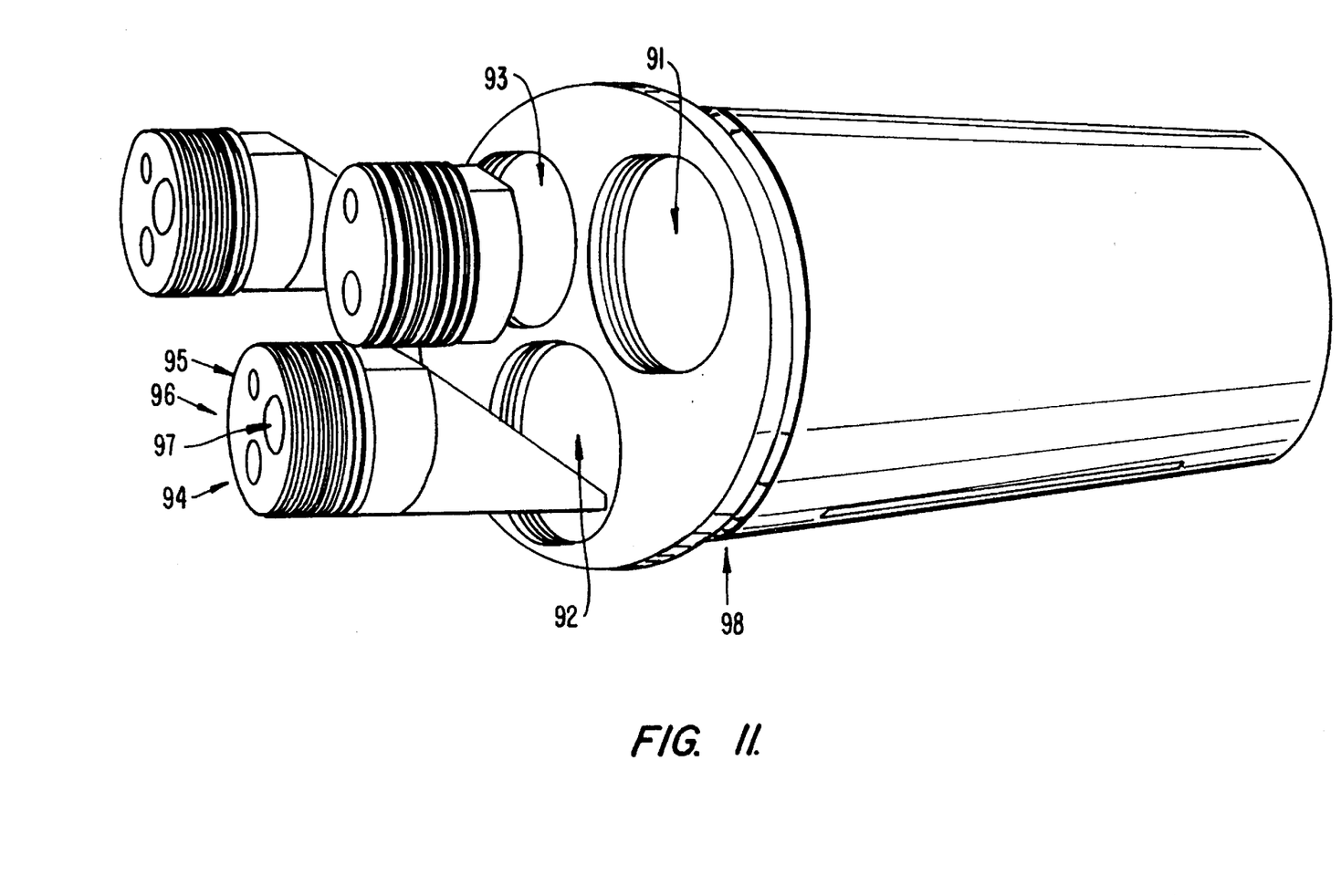
FIG. 11 illustrates one embodiment for a sensor probe.

FIG. 11 illustrates one embodiment for a sensor probe 82 for use with the invention. The probe contains three cells; the reference cell 91, the sample cell 92 for measuring the oxygen content of the ullage of the fuel tank to which the probe is fitted, and sample cell 93 for measuring the oxygen content of the on-board inert gas generation system (OBIGGS). Each cell contains a transmit port 94 through which the laser beam enters the cell. After the laser beam passes through the medium twice, it exits through a receiver port 95. Each cell contains a temperature port 96 into which a temperature probe is fitted. The two sample cells, 92 and 93, also have ports 97 for pressure probes. Since the reference cell is sealed, it does not contain a pressure port. In this embodiment the probe is sealed to the fuel tank by an O-ring 98.

Figure 12:
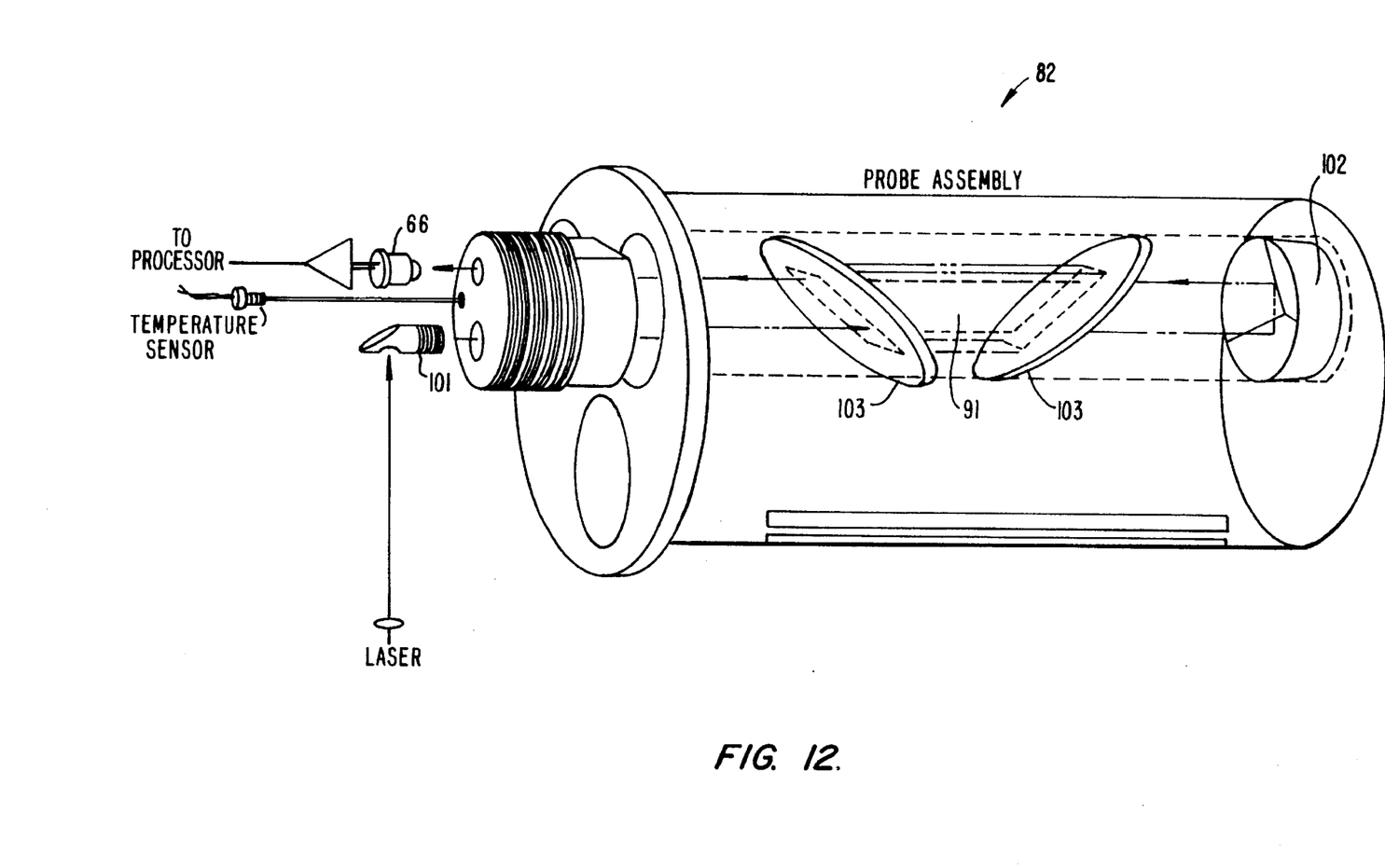
FIG. 12 shows additional detail of cell 91.

FIGS. 12–15 show further detail of cells 91, 92, and 93. For each cell the laser beam enters via a turning and alignment mirror 101. After passing initially through the medium, the medium being that of either a sample gas or of the reference, the laser beam is reflected by a retro-reflector 102. The beam then passes through the medium a second time, thus doubling the path length, prior to being detected by detector 66. Reference cell 91 is shown in FIG. 12. Cell 91 is permanently sealed on either end by windows 103. The windows are set at Brewster's angle to minimize reflections and maximize the beam intensity through the medium. The windows as well as the other optical components in the preferred embodiment are coated with an anti-reflection dielectric film to further minimize reflection losses.

Figure 13:
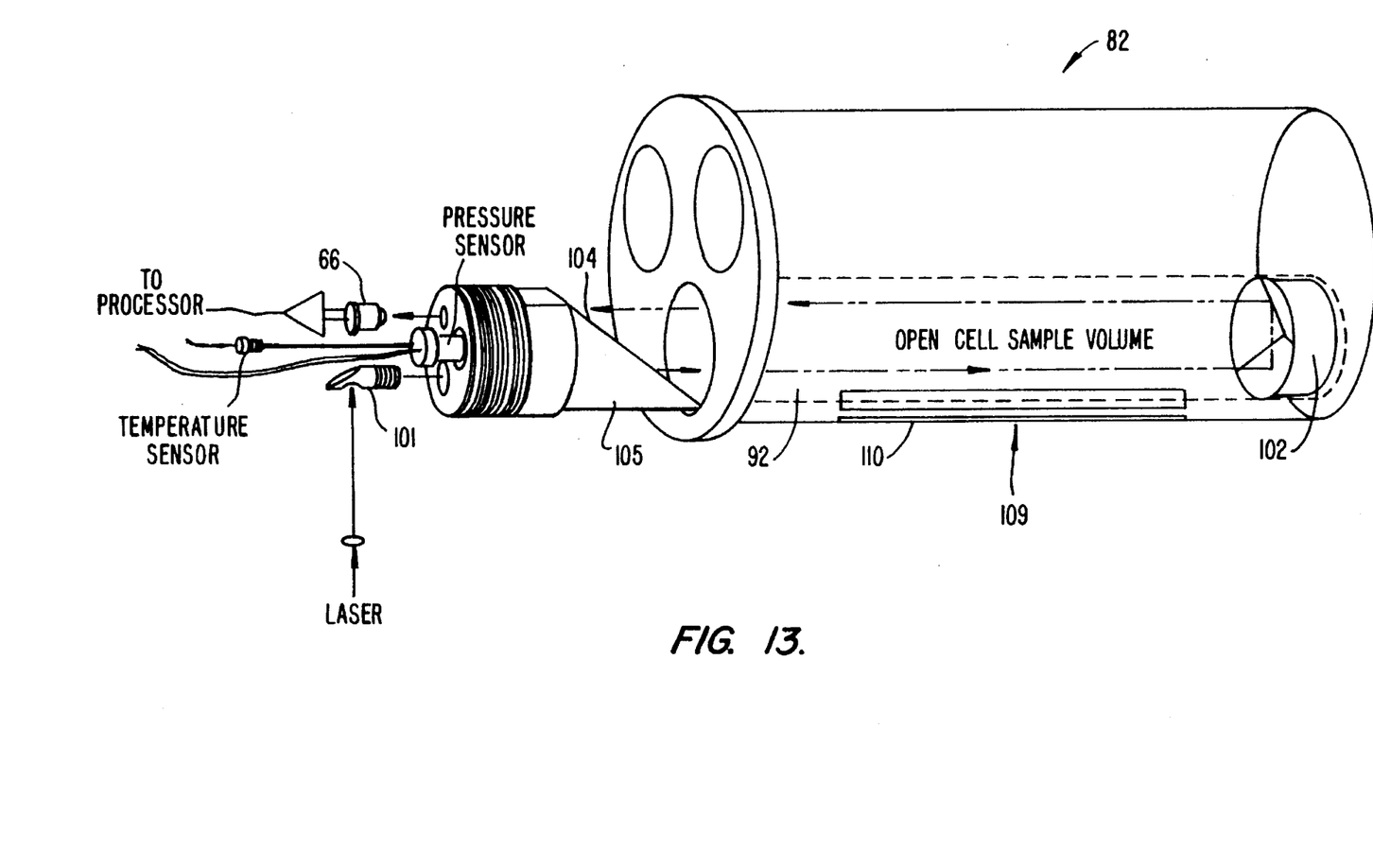
FIG. 13 shows additional detail of cell 92.
Figure 14:
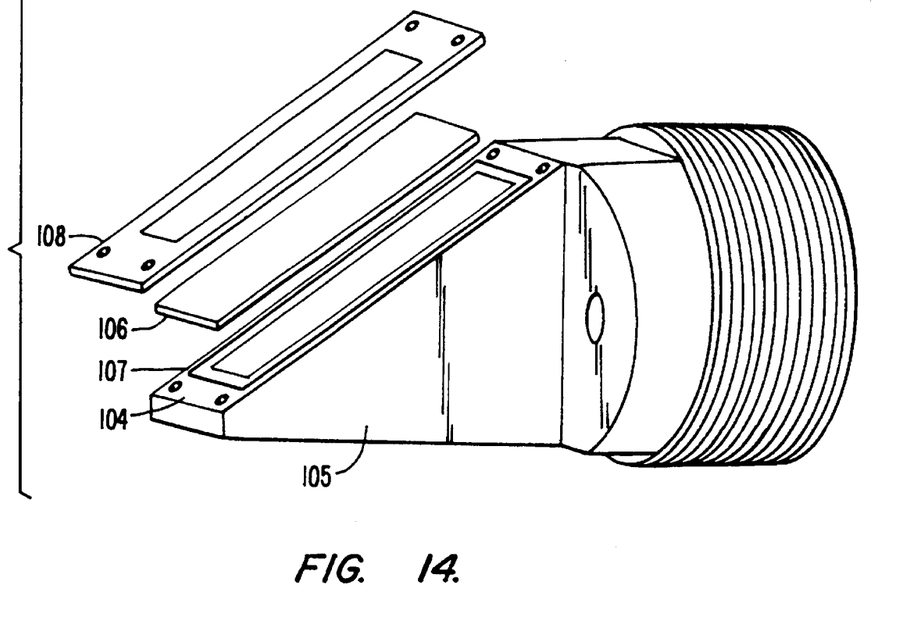
FIG. 14 is a detailed view of flange 105.

FIG. 13 shows additional detail of fuel vapor sample cell 92. Attached to face 104 of flange 105 is an anti-reflection coated window 106 set at Brewster's angle. Additional detail of flange 105 is shown in FIG. 14. Window 106 is sealed against face 104 with an O-ring 107. The window is held in place with a retainer 108. Fuel tank vapor enters the cells via vapor ports 109. Ports 109 are covered with a vapor permeable film 110 to prevent liquid fuel from entering cell 92.

Figure 15:
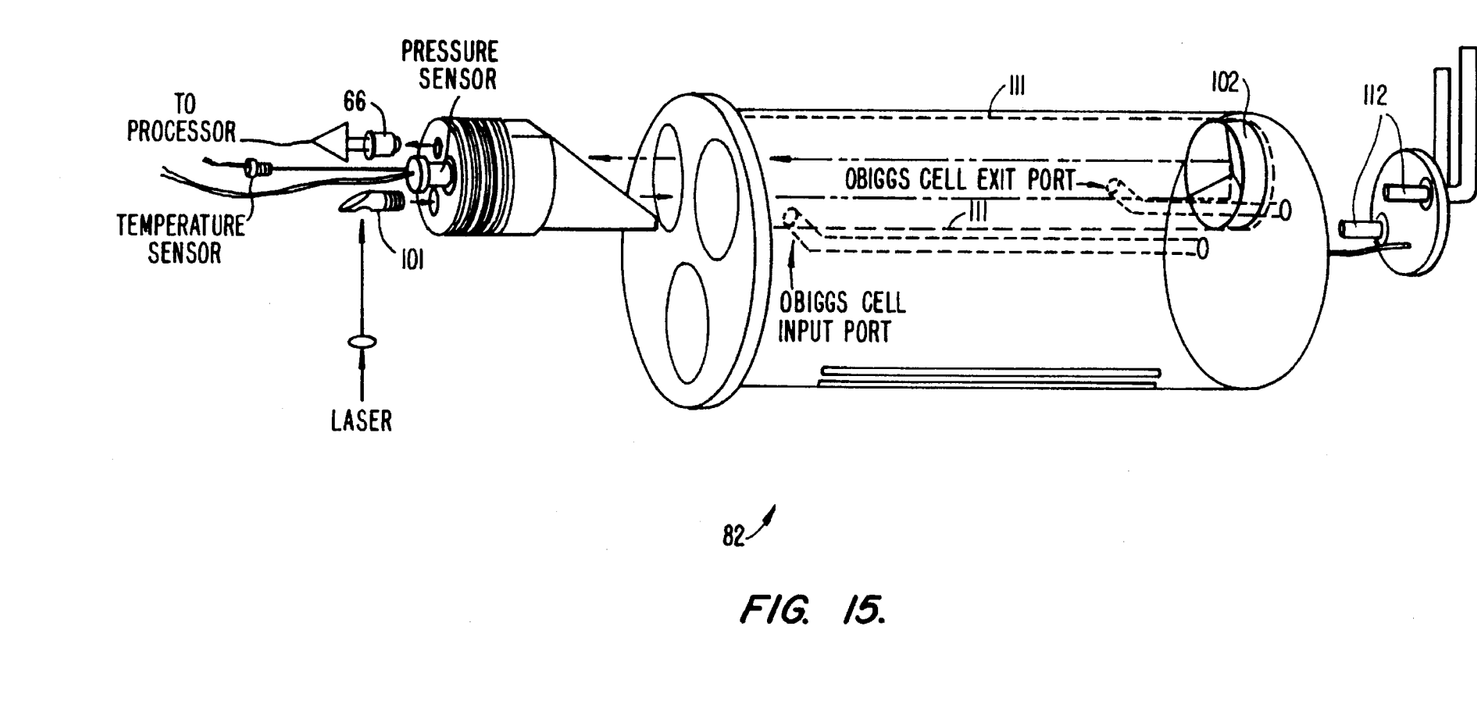
FIG. 15 shows additional detail of cell 93.

FIG. 15 shows additional detail of sample cell 93 used in the preferred embodiment to monitor the oxygen concentration in the OBIGGS system. The OBIGGS cell is a sealed cell within probe 82 and is schematically illustrated in FIG. 10C by dashed lines 111. Vapor from the OBIGGS system enters and exits cell 93 through lines 112.

SPECTROSCOPIC MEASUREMENT OF TEMPERATURE AND PRESSURE

In addition to the measurement of molecular oxygen, the sensor described in this invention is capable of determining the pressure and temperature of the gas sample spectroscopically. Because the width and strength of the oxygen absorption lines vary with pressure and temperature in a known way, accurate measurement of the line widths and intensities of two different oxygen absorption lines allows the temperature and pressure to be determined. The line width effect is due to broadening of the molecular electronic transition by collisions with other molecules, and is the dominant broadening effect for pressures ranging from around 20 torr up to many atmospheres. The line strength effect is due to the fact that the ground state of the transition responsible for each oxygen absorption line in the 760 nm region corresponds to a different molecular rotational level, and at any given temperature the ground state population is different for the different rotational levels. Since the line strength is proportional to the ground state population, it is temperature dependent in a way that depends on the ground state energy.

The width $\gamma$ of an oxygen absorption line in the collisionally (pressure) broadened regime is given by $$\gamma(T,P) = \gamma(T_o,P_o)(P/P_o)(T_o/T)^{1-n}$$

and the absorption cross-section is given by $$\sigma(T,P) = \sigma(T_o,P_o)(P_o/P)(T_o/T)^n \exp\{-E_o(1/kT - 1/kT_o)\}$$

If a measurement is made of the absorption of two different oxygen lines from the same gas sample, then the ratio of the two absorptions is given by $$\begin{aligned} R &= W_i/W_j = J(T,P)GN(T,P)\,\sigma_i(T,P)D/J(T,P)GN(T,P)\,\sigma_j(T,P)D \\ &= \sigma_i(T,P)/\sigma_j(T,P) \\ &= \{\sigma_i(T_o,P_o)/\sigma_j(T_o,P_o)\}\exp\{-(E_{oi} - E_{oj})(1/kT - 1/kT_o)\} \end{aligned}$$

The sample temperature is then given by $$T = \{(1/T_o) + [k/(E_{oi} - E_{oj})]\ln(\sigma_{oi}W_j/\sigma_{oj}W_i)\}^{-1}$$

Since the ground stage energies $E_{oi}$ and $E_{oj}$ of the two lines are known, as is the reference temperature $T_o$, and the cross sections $\sigma_{oi}$ and $\sigma_{oj}$ at the reference temperature, the sample temperature T can be determined from measurement of the signal ratio using the above expression. For example, if we choose to monitor the oxygen lines at 761.42 nm and 761.73 nm, which have ground state energies of 16.388 $cm^{-1}$ and 662.103 $cm^{-1}$ respectively, then a simple error analysis shows that a 1% uncertainty in the absorption ratio results in a 1° K. temperature measurement error at 300° K.

Once the temperature of the sample is measured, the pressure may be determined from the width of the absorption using the above expression for γ. In practice, the linewidth is measured by repetitively ramping the diode laser mode over the absorption line and digitizing and averaging the resulting waveform. The recovered waveform is then parametrically fit using non-linear least squares techniques to the known functional form for the lineshape. The output of this fit is the linewidth. This linewidth is then inserted in the above expression for γ which is then solved for pressure. Since the linewidth is linear in pressure, a 1% error in the linewidth measurement yields a 1% error in the pressure determination.

CONCLUSION

In summary, it can be seen that the present invention provides a means of accurately measuring the oxygen concentration in an environment which is potentially hostile to electronics as well as one in which the temperature and pressure are widely fluctuating. While the above is a complete description of specific embodiments, alternative constructions, modifications, and equivalents may be used. For example, a modulation frequency other than 10 MHz can be used.

Therefore, the above description should not be taken as limiting the scope of the invention which is defined by the claims.

We claim:

1. Apparatus for determining oxygen concentration in an aircraft fuel tank, comprising:

at least one sample cell for holding gas samples to be analyzed, said sample cell attached to said fuel tank;

a reference cell for holding a volume of gas having a known oxygen concentration;

a laser diode illuminator for passing light of wavelength in the 0.75 micrometer to 0.77 micrometer range through each sample cell and said reference cell, wherein said wavelength is at an absorption line for oxygen molecules;

means for determining pressure in each cell;

means for determining temperature in each cell;

means for modulating the light at said wavelength according to a first regime;

means for demodulating the light at said wavelength according to a second regime to provide respective signals corresponding to the absorption at said wavelength in each of said sample and reference cells;

means for correcting said respective signals for the pressure and temperature determined for each cell; and means for correlating said corrected respective signals to provide a representation of the concentration of oxygen in said fuel tank.

2. The apparatus of claim 1 wherein each cell is coupled to said laser diode illuminator by a fiber optic link, said laser diode illuminator remotely mounted away from said fuel tank.

3. The apparatus of claim 1 wherein at least one sample cell has an open sample volume.

4. The apparatus of claim 3 wherein said sample cell is covered with a gas permeable cover.

5. The apparatus of claim 1 wherein the pressure in the reference cell is determined by measuring the temperature in the reference cell.

6. The apparatus of claim 1 wherein the temperature in the sample cell is determined spectroscopically by measuring signals corresponding to the absorption of at least two oxygen absorption lines, ratioing said signals, and determining said temperature using known spectroscopic characteristics of said oxygen absorption lines.

7. The apparatus of claim 1 wherein:

said means for modulating comprises means for modulating the light of a given optical frequency at a single RF modulation frequency to produce multiple sidebands displaced from the optical frequency by integral multiples of said single modulation frequency; and said means for demodulating comprises means for detecting a signal at an integral multiple of the single modulation frequency.

8. The apparatus of claim 1 wherein said RF modulation frequency is 10 MHz.

9. A method of determining oxygen concentration in a molecular gas sample comprising:

passing light emanating from a laser diode of a wavelength in the 0.75 micrometer to 0.77 micrometer range through a sample cell, said sample cell containing a volume of said molecular gas sample;

passing light emanating from said laser diode through a reference cell, said reference cell holding a volume of gas having a known oxygen concentration;

determining pressure in said reference cell;

determining temperature in said reference cell;

modulating said light according to a first regime;

demodulating said light according to a second regime and providing a first signal corresponding to the absorption of said light passing through said sample cell at a first absorption line, a second signal corresponding to the absorption of said light passing through said sample cell at a second absorption line, a third signal corresponding to the absorption of said light passing through said reference cell at said first absorption line, and a fourth signal corresponding to the absorption of said light passing through said reference cell at said second absorption line;

determining the temperature in said sample cell spectroscopically from said signals and said reference cell temperature;

measuring the absorption linewidth for said first and second absorption lines in said sample and reference cells;

determining the pressure in said sample cell from said absorption linewidths, said temperature of said reference cell, said temperature of said sample cell, and said pressure of said reference cell; and determining the oxygen concentration in said sample cell from said signals, wherein said signals are corrected for the pressure and temperature determined for each cell.

10. The method according to claim 9, wherein:

said modulating step comprises modulating the light of a given optical frequency at a single RF modulation frequency to produce multiple sidebands displaced from the optical frequency by integral multiples of said single modulation frequency; and said demodulating step comprises detecting a signal at an integral multiple of the single modulation frequency.

11. A method of determining oxygen concentration in an aircraft fuel tank, comprising:

passing light emanating from a laser diode of a wavelength in the 0.75 micrometer to 0.77 micrometer range through a molecular gas sample, said sample taken from said fuel tank, wherein said wavelength is at an absorption line for oxygen molecules;

passing light emanating from said laser diode at said wavelength through a reference cell, said reference cell holding a volume of gas having a known oxygen concentration;

determining temperature in said reference cell and in said molecular gas sample;

determining pressure in said reference cell and in said molecular gas sample;

modulating said light at said wavelength according to a first regime;

demodulating said light at said wavelength according to a second regime and providing a first signal corresponding to the absorption of said light passing through said sample and a second signal corresponding to the absorption of said light passing through said reference cell;

correcting said first and second signals for the determined pressures and temperatures; and determining the oxygen concentration in said fuel tank from said corrected first and second signals.

12. The method of claim 11, wherein said gas sample is contained in a sample cell, said sample cell attached to said fuel tank.

13. The method of claim 12, further comprising the step of connecting said laser diode to said sample cell and said reference cell via fiber optics.

14. The method of claim 11, further comprising the steps of:

providing a third signal corresponding to the absorption passing through said sample at a second absorption line, wherein said first signal corresponds to the absorption passing through said sample at a first absorption line;

providing a fourth signal corresponding to the absorption passing through said reference cell at a second absorption line, wherein said second signal corresponds to the absorption passing through said reference cell at a first absorption line;

using said signals and said reference cell temperature to determine the temperature in said sample;

measuring the absorption linewidth for said first and second absorption lines in said sample and said reference cell; and, using said absorption linewidths, said temperature of said reference cell, said temperature of said sample cell, and said pressure of said reference cell to determine the pressure in said sample.

15. The method of claim 11, wherein said modulating step comprises modulating the light of a given optical frequency at a single RF modulation frequency to produce multiple sidebands displaced from the optical frequency by integral multiples of said single modulation frequency and said demodulating step comprises detecting a signal at an integral multiple of the single modulation frequency.

* * * * *